United States Patent
Kufer et al.

(10) Patent No.: US 9,486,475 B2
(45) Date of Patent: Nov. 8, 2016

(54) PPS FOR THE PREVENTION OF POTENTIAL ADVERSE EFFECTS CAUSED BY CD3 SPECIFIC BINDING DOMAINS

(71) Applicant: AMGEN RESEARCH (MUNICH) GMBH, Munich (DE)

(72) Inventors: Peter Kufer, Munich (DE); Dirk Nagorsen, Munich (DE); Juergen Scheele, Munich (DE); Gerhard Zugmaier, Munich (DE); Matthias Klinger, Gilching (DE); Patrick Hoffmann, Bad Heilbrunn (DE); Virginie Naegele, Munich (DE); Elaine-Pashupati Dopfer, Munich (DE)

(73) Assignee: AMGEN RESEARCH (MUNICH) GMBH, Munich (DE)

(*) Notice: Subject to any disclaimer, the term of this patent is extended or adjusted under 35 U.S.C. 154(b) by 0 days.

(21) Appl. No.: 14/176,089

(22) Filed: Feb. 8, 2014

(65) Prior Publication Data
US 2014/0228316 A1 Aug. 14, 2014

Related U.S. Application Data

(60) Provisional application No. 61/762,718, filed on Feb. 8, 2013.

(51) Int. Cl.
*A01N 43/04* (2006.01)
*A61K 31/715* (2006.01)
*A61K 31/737* (2006.01)

(52) U.S. Cl.
CPC .................. *A61K 31/737* (2013.01)

(58) Field of Classification Search
CPC .................................................. A61K 31/737
See application file for complete search history.

(56) References Cited

U.S. PATENT DOCUMENTS

| | | | |
|---|---|---|---|
| 2,689,848 A | 9/1954 | Husemann et al. | |
| 2009/0047243 A1* | 2/2009 | Rickles et al. | 424/85.2 |
| 2009/0053168 A1* | 2/2009 | Rickles et al. | 424/85.2 |
| 2010/0105889 A1 | 4/2010 | Deshpande et al. | |
| 2014/0099254 A1* | 4/2014 | Chang et al. | 424/1.11 |
| 2014/0227272 A1* | 8/2014 | Kufer et al. | 424/135.1 |

FOREIGN PATENT DOCUMENTS

| | | |
|---|---|---|
| EP | 623679 A1 | 11/1994 |
| WO | WO-99/54440 A1 | 10/1999 |
| WO | WO-2004/106381 A1 | 12/2004 |
| WO | WO-2007/068354 A1 | 6/2007 |
| WO | WO-2007/131092 A2 | 11/2007 |
| WO | WO-2007/147090 A2 | 12/2007 |
| WO | WO-2008/119565 A2 | 10/2008 |
| WO | WO-2008/119566 A2 | 10/2008 |
| WO | WO-2008/119567 A2 | 10/2008 |
| WO | WO-2011/051307 A1 | 5/2011 |

OTHER PUBLICATIONS (R) Merck Index, 14th. Ed., 2006, Merck & Co., Whitehouse Station, New Jersey, see p. 1231, Entry No. 7134 ; see "Pentosan Polysulfate" and the sodium salt thereof.*
Baaten et al., Regulation of Antigen-Experienced T Cells: Lessons from the Quintessential Memory Marker CD44. *Front Immunol.* 3: 23 (2012).
Bargou et al., Tumor regression in cancer patients by very low doses of a T cell-engaging antibody. *Science* 321: 974-7 (2008).
Bucolo et al., New coumarin-based anti-inflammatory drug: putative antagonist of the integrins alphaLbeta2 and alphaMbeta2. *J. Pharm. Pharmacol.* 60(11): 1473-9 (2008).
Crick, Codon—anticodon pairing: the wobble hypothesis. *J. Mol. Biol.* 19: 548-55 (1966).
Curley et al., Integrin antagonists. *Cell. Mol. Life Sci.* 56: 427-41 (1999).
Ding et al., Regulation of chemokine-induced transendothelial migration of T lymphocytes by endothelial activation: differential effects on naive and memory T cells. *J. Leukoc. Biol.* 67(6): 825-33 (2000).
Eylar et al., Sustained levels of ascorbic acid are toxic and immunosuppressive for human T cells. *P R Health Sci. J.* 15: 21-6 (1996).
Fabene et al., A role for leukocyte-endothelial adhesion mechanisms in epilepsy. *Nat. Med.* 14: 1377-83 (2008).
Fagan et al., Minocycline to improve neurologic outcome in stroke (MINOS): A dose-finding study. *Stroke* 41: 2283-7 (2010).
Feigelson et al., The Src kinase p56(lck) up-regulates VLA-4 integrin affinity. Implications for rapid spontaneous and chemokine-triggered T cell adhesion to VCAM-1 and fibronectin. *J. Biol. Chem.* 276: 13891-901 (2001).
Feng et al., Endogenous PMN sialidase activity exposes activation epitope on CD11b/CD18 which enhances its binding interaction with ICAM-1. *J. Leukoc. Biol.* 90: 313-21 (2011).
Fiedler et al., Angiopoietins: A link between angiogenesis and inflammation. *Trends Immunol.* 27: 552-8 (2006).

(Continued)

*Primary Examiner* — Lawrence E Crane
(74) *Attorney, Agent, or Firm* — Marshall, Gerstein & Borun LLP

(57) ABSTRACT

The present invention relates to a pentosanpolysulfate (PPS) or a pharmaceutically acceptable salt thereof for use in the amelioration, treatment, or prevention of adverse neurological events caused by administering an antibody or fragment thereof comprising a CD3 binding domain, including a CD19 x CD3 bispecific single chain antibody, such as blinatumomab. PPS is a semi-synthetically produced heparin-like macromolecular carbohydrate derivative, which chemically and structurally resembles glycosaminoglycans. Kits comprising a PPS, an antibody or fragment thereof comprising a CD3 binding domain, and instructions for administration, which indicate that the PPS is to be employed for the amelioration, treatment or prevention of adverse neurological events caused by administering the antibody or fragment thereof comprising said CD3 binding domain, are also disclosed.

14 Claims, No Drawings

(56) References Cited

OTHER PUBLICATIONS

GenBank Accession No. AAA69966, CD19 [*Homo sapiens*], dated Jul. 18, 1995.
GenBank Accession No. NM_000733, *Homo sapiens* CD3e molecule, epsilon (CD3-TCR complex) (CD3E), mRNA, dated Mar. 24, 1999.
Gerli et al., Salicylates inhibit T cell adhesion on endothelium under nonstatic conditions: Induction of L-selectin shedding by a tyrosine kinase-dependent mechanism. *J. Immunol.* 166(2): 832-40 (2001).
Grupp et al., Chimeric antigen receptor-modified T cells for acute lymphoid leukemia. *N. Engl. J. Med.* 368(16): 1509-18 (2013).
Haanstra et al., Antagonizing the α4β1 integrin, but not α4β7, inhibits leukocytic infiltration of the central nervous system in rhesus monkey experimental autoimmune encephalomyelitis. *J. Immunol.* 190(5): 1961-73 (2013).
Hirota-Takahata et al., F-19848 A, a novel inhibitor of hyaluronic acid binding to cellular receptor CD44. *J. Antibiot.* (Tokyo) 60: 633-9 (2007).
Höpfner et al., Selectin-blocking semisynthetic sulfated polysaccharides as promising anti-inflammatory agents. *J. Pharm. Pharmacol.* 55: 697-706 (2003).
Hosse et al., A new generation of protein display scaffolds for molecular recognition. *Protein Sci.* 15:14-27 (2006).
Kabat et al., Sequences of Proteins of Immunological Interest, 5th Ed. U.S. Department of Health and Human Services, Public Health Services National Institutes of Health (1991).
Kivisäkk et al., Human cerebrospinal fluid central memory CD4+ T cells: evidence for trafficking through choroid plexus and meninges via P-selectin. *Proc. Natl. Acad. Sci. USA*, 100: 8389-94 (2003).
Kling et al., Pharmacological control of platelet-leukocyte interactions by the human anti-P-selectin antibody inclacumab—preclinical and clinical studies. *Thromb. Res.* 131(5): 401-10 (2013).
Kochenderfer et al., Treating B-cell cancer with T cells expressing anti-CD19 chimeric antigen receptors. *Nat. Rev. Clin. Oncol.* 10(5): 267-76 (2013).
Koszik et al., Efalizumab modulates T cell function both in vivo and in vitro. *J. Dermatol. Sci.* 60: 159-66 (2010).
Ku et al., Concentration dependent anti-inflammatory effects thrombin on polyphosphate-mediated inflammatory responses in vitro and in vivo. *Inflamm. Res.* 62(6): 609-16 (2013).
Lampl et al., Minocycline treatment in acute stroke: An open-label, evaluator-blinded study. *Neurology* 69: 1404-10 (2007).
Lefer, Pharmacology of selectin inhibitors in ischemia/reperfusion states. *Ann. Rev. Pharmacol. Toxicol.* 40: 283-94 (2010).
Mobley et al., Measurement of cellular adhesion under static conditions. *Curr. Protoc. Immunol.* Chapter 7: Unit 7.28 (2001).
Moore, Structure and function of P-selectin glycoprotein ligand-1. *Leuk. Lymphoma* 29: 1-15 (1998).
Murai et al., CD44-chondroitin sulfate interactions mediate leukocyte rolling under physiological flow conditions. *Immunol. Lett.* 93: 163-70 (2004).
Needleman et al., A general method applicable to the search for similarities in the amino acid sequence of two proteins. *J. Mol. Biol.* 48: 443-53 (1970).
Nicaise et al., Affinity transfer by CDR grafting on a nonimmunoglobulin scaffold. *Protein Sci.* 13: 1882-91 (2004).
Nikodemova et al., Minocycline attenuates experimental autoimmune encephalomyelitis in rats by reducing T cell infiltration into the spinal cord. *J. Neuroimmunol.* 219: 33-7 (2010).
Nygren et al., Scaffolds for engineering novel binding sites in proteins. *Curr. Opin. Struct. Biol.* 7: 463-9 (1997).
Offner et al., Induction of regular cytolytic T cell synapses by bispecific single-chain antibody constructs on MHC class I-negative tumor cells. *Mol. Immunol.* 43: 763-71 (2006).
Osaka et al., In vivo imaging of leukocyte recruitment to the atheroprone femoral artery reveals anti-inflammatory effects of rosuvastatin. *Biomed. Res. Int.* 2013: 962369 (2013).
Porter et al., Chimeric antigen receptor-modified T cells in chronic lymphoid leukemia. *N. Engl. J. Med.* 365: 725-33 (2011).
Pullen et al., Pharmacological characterization of PF-00547659, an anti-human MAdCAM monoclonal antibody. *Br. J. Pharmacol.* 157: 281-93 (2009).
Rao et al., Delivery of SAR 1118 to the retina via ophthalmic drops and its effectiveness in a rat streptozotocin (STZ) model of diabetic retinopathy (DR). *Invest. Ophthalmol. Vis. Sci.* 51: 5198-204 (2010).
Rohnelt et al., Immunosurveillance modelled in vitro: naive and memory T cells spontaneously migrate across unstimulated microvascular endothelium. *Int. Immunol.* 9(3): 435-50 (1997).
Skerra, Alternative non-antibody scaffolds for molecular recognition. *Curr. Opin. Biotechnol.* 18: 295-304 (2007).
Smith et al., Comparison of biosequences. *Adv. Appl. Math.* 2: 482-9 (1981).
Stefanich et al., A humanized monoclonal antibody targeting the β7 integrin selectively blocks intestinal homing of T lymphocytes. *Br. J. Pharmacol.* 162: 1855-70 (2011).
Thomas et al., Targeting leukocyte migration and adhesion in Crohn's disease and ulcerative colitis. *Inflammopharmacology* 20: 1-18 (2012).
Topp et al., Targeted therapy with the T-cell-engaging antibody blinatumomab of chemotherapy-refractory minimal residual disease in B-lineage acute lymphoblastic leukemia patients results in high response rate and prolonged leukemia-free survival. *J. Clin. Oncol.* 29: 2493-8 (2011).
Valignat et al., T lymphocytes orient against the direction of fluid flow during LFA-1-mediated migration. *Biophys. J.* 104(2): 322-31 (2013).
Van Deventer et al., A phase II dose ranging, double-blind, placebo-controlled study of alicaforsen enema in subjects with acute exacerbation of mild to moderate left-sided ulcerative colitis. *Aliment. Pharmacol. Ther.* 23: 1415-25 (2006).
Weeks et al., Natramune and PureWay-C reduce xenobiotic-induced human T-cell alpha5beta1 integrin-mediated adhesion to fibronectin. *Med. Sci. Monit.* 14: BR279-85 (2008).
Welzenbach et al., Small molecule inhibitors induce conformational changes in the I domain and the I-like domain of lymphocyte function-associated antigen-1. Molecular insights into integrin inhibition. *J. Biol. Chem.* 277: 10590-8 (2002).
Yi et al., Astilbin inhibits the adhesion of T lymphocytes via decreasing TNF-alpha and its associated MMP-9 activity and CD44 expression. *Int. Immunopharmacol.* 8: 1467-74 (2008).
Zhang et al., Pilot study of minocycline in relapsing-remitting multiple sclerosis. *Can. J. Neurol. Sci.* 35: 185-91 (2008).
Kadmiel et al., Glucocorticoid receptor signaling in health and disease. *Trends Pharmacol. Sci.* 34(9): 518-30 (2013).

* cited by examiner

PPS FOR THE PREVENTION OF POTENTIAL ADVERSE EFFECTS CAUSED BY CD3 SPECIFIC BINDING DOMAINS

CROSS-REFERENCE TO RELATED APPLICATION

This application claims the priority benefit of U.S. Provisional Patent Application No. 61/762,718, filed Feb. 8, 2013.

The entire contents of the ASCII text entitled "48405_seq_Listing.txt," created on Feb. 7, 2014, and having a size of 16 kilobytes is incorporated herein by reference.

The present invention relates to pentosanpolysulfate (PPS) for use in the amelioration, treatment or prophylaxis of neurological adverse events caused by a CD3 binding domain. Kits comprising pentosanpolysulfate, a CD3 binding domain and instructions for use which indicate that the pentosanpolysulfate is to be employed for the treatment amelioration and/or prophylaxis of neurological adverse events caused by said CD3 binding domain, are also disclosed.

Antibody-based cancer therapies require a target antigen firmly bound to the surface of cancer cells in order to be active. By binding to the surface target, the antibody can directly deliver a deadly signal to the cancer cell or indirectly by, for example, recruiting a cytotoxic T cell, if it is a bispecific antibody. In an ideal treatment scenario, a target antigen is abundantly present and accessible on every cancer cell and is absent, shielded or much less abundant on normal cells. This situation provides the basis for a therapeutic window in which a defined amount of the antibody-based therapeutic effectively hits cancer cells but spares normal cells.

Though binding domains like antibodies are an effective means in treating many disorders, in particular cancer, their administration is not necessarily devoid of side effects. Adverse effects may cause a reversible or irreversible change in the health status of a patient. As adverse effects could be harmful and undesired, it is highly desirable to avoid them. However, though it is known that a medicament can cause adverse effects, its prescription and administration could not be avoided or is accepted, since the medicament has an outstanding beneficial therapeutic effect or may even be life-saving.

In clinical trials, a general distinction can be made between adverse effects (AEs) and serious adverse effects (SAEs). Specifically, adverse effects can be classified in 5 grades in accordance with the Common Terminology Criteria for Adverse Events (CTCAE). Grade 1 relates to mild AE, Grade 2 to moderate AE, Grade 3 to severe AE, Grade 4 to life-threatening or disabling AE, while Grade 5 means death related to AE.

An adverse effect observed in antibody therapy is the occurrence of infusion-related side effects, such as the cytokine release syndrome ("CRS"). Other adverse side effects described to be associated with CRS are fatigue, vomiting, tachycardia, hypertension, back pain, but also central nervous system reactions (CNS reactions), such as seizures, encephalopathy, cerebral edema, aseptic meningitis, and headache.

Adverse events such as cytokine release and neurological reactions have not only been observed with antibodies binding to the T cell receptor but also with a CD19xCD3 bispecific single chain antibody binding to the CD3 part of the T cell receptor (called Blinatumomab (MT103)). Blinatumomab (MT103) is a lymphoma-directed, recombinant bispecific single-chain CD19xCD3 antibody that binds to CD19 on the surface of almost all B cells and B tumor cells and concomitantly can engage a T cell, thereby triggering the T-cell to kill the target B cell or B tumor cell. Blinatumomab consists of four immunoglobulin variable domains assembled into a single polypeptide chain. Two of the variable domains form the binding site for CD19, a cell surface antigen expressed on most B cells and B tumor cells. The other two variable domains form the binding site for the CD3 complex on T cells. Blinatumomab is designed to direct the body's cytotoxic, or cell-destroying, T cells against tumor cells, and represent a new therapeutic approach to cancer therapy. Blinatumomab is presently in clinical trials.

As described for instance in WO 99/54440, adverse effects have been observed in a previous study performed with Blinatumomab applied in repeated bolus infusions to a patient with B-cell derived chronic lymphatic leukemia (B-CLL). As shown in FIGS. 19 and 20 of WO 99/54440, release of TNF, IL-6 and IL-8 has been found in response to each of the two microgram of the administered 20 minute-infusions of 3 microgram and 10 microgram mentioned bispecific single chain antibody, respectively, with cytokine release after each administration. Maximal cytokine release was observed after microgram of bispecific single chain antibody. In administration of 10 microgram following clinical trial studies, in which escalating doses of the CD19xCD3 bispecific single chain antibody have been administered to patients with B cell malignancies as bolus infusions, adverse effects have also been observed. According to a retrospective analysis, 7 out of 22 patients showed an early neurological reaction, including, for example, confusion, ataxia, speech disorder, or disorientation.

As shown in Bargou et al. (Science 321 (2008): 974-7), doses as low as 0.005 milligrams per square meter per day continuously administered to non-Hodgkin's lymphoma patients over four weeks led to an elimination of lymphoma target cells in blood. Partial and complete tumor regressions were first observed at a dose level of 0.015 milligrams/m$^2$/d, and all seven patients treated at a dose level of 0.06 milligrams/m$^2$/d experienced a tumor regression (Bargou et al., cited above). The CD19xCD3 bispecific single chain antibody also led to clearance of tumor cells from bone marrow and liver. However, though this (still ongoing) study established clinical proof of concept for the therapeutic potency of the CD19xCD3 bispecific single chain antibody format in the treatment of blood-cell derived cancer, neurological reactions have been found in the course of the aforementioned clinical trial. In order to get these undesired side effects under control, the mode of administration of the CD19xCD3 bispecific single chain antibody has been changed in that it has been switched over from bolus infusion to a continuous intravenous administration of said antibody for a longer period of time. Accordingly, since Blinatumomab is a very promising candidate medicament for treating non-Hodgkin's lymphoma (NHL), acute lymphoblastic leukemia (ALL), chronic lymphocytic leukemia (CLL) and/or mantle cell lymphoma, it is highly desirable to reduce or even completely avoid undesired side-effects in the treatment of patients in need thereof with the CD19xCD3 bispecific single chain antibody.

It is however difficult to design a CD19xCD3 antibody-based therapy, which does not cause CNS (neurological) reactions including neurological reactions, or, to put it differently, it is desired to provide a CD19xCD13 antibody-based medical therapies with increased patient tolerability, i.e., reduced or even no undesired adverse effects such as CNS reactions.

Though pharmaceutical means and methods which allow a more gradual activation of T cell populations (see WO 2007/068354) already helped to avoid significant adverse side effects in patients treated with the CD19xCD3 bispecific single chain antibody, neurological reactions could unfortunately not be prevented by these measures, in particular in cases in which doses of more than 5 to 10 microgram per square meter per day (i.e. 24 h) of the antibody have been administered.

Thus, the technical problem underlying the present invention was to provide means and methods to overcome the above problems.

The present invention addresses this need and thus provides embodiments concerning means and methods for use in the amelioration, treatment or prophylaxis of neurological adverse effects caused by a CD3 binding domain, such as a CD19xCD3 bispecific antibody.

These embodiments are characterized and described herein and reflected in the claims.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In view of the adverse events described in the sections above, particularly the adverse CNS effects including neurological reactions observed with CD3 specific binding domains, the finding that these adverse effects can be mitigated or even prevented if the administration of the CD3-specific binding domain is accompanied or preceded by the administration of a pentosanpolysulfate, is definitely remarkable.

Specifically, the present inventors observed that those patients, to whom a CD19xCD3 bispecific antibody was administered, encountered neurological side effects, and, further, that these neurological side effects could be prevented or alleviated by means of a pentosanpolysulfate (PPS) therapy.

Accordingly, the present invention establishes for the first time that a pentosanpolysulfate (PPS) such as pentosanpolysulfate sodium (e.g., pentosanpolysulfate SP 54) mitigate or even prevent neurological adverse effects which might occur in the course of a treatment with CD3 specific binding domains (see also the Example section).

Pentosanpolysulfate ($C_{14}H_{26}O_{21}S_4$), also known as Pentosan polysulphate, Xylan Hydrogen Sulfate, Xylan Polysulfate, is a semi-synthetically produced heparin-like macromolecular carbohydrate derivative, which chemically and structurally resembles glycosaminoglycans. It is a white odorless powder, slightly hygroscopic and soluble in water to 50% at pH 6. It has a molecular weight of 4000 to 6000 Dalton.

PPS is, for example, sold under the name Elmiron® by Ortho-McNeil Pharmaceutical, inc. and is thus far the only oral medication approved by the U.S. FDA for the treatment of interstitial cystitis, also known as painful bladder syndrome. For that application PPS is administered orally, however, it can alternatively be administered intravenously.

In a first embodiment, the present invention relates to a pentosanpolysulfate for use in the amelioration, treatment or prophylaxis of neurological adverse effects caused by a CD3 binding domain. As outlined above, these unwanted adverse effects frequently accompany a therapy with a CD3 binding domain. The present invention remedies these disadvantages and provides a PPS for use in the amelioration, treatment or prophylaxis of neurological adverse effects in a patient wherein said patient is subject to therapy with a CD3 binding domain.

The present invention thus relates to pentosanpolysulfate for use in the amelioration, treatment or prophylaxis of neurological adverse effects caused by a CD3 binding domain in a human patient, wherein said pentosanpolysulfate is to be administered prior to, concurrently with and/or subsequently to the administration of said binding domain.

The neurological side effects are "caused by" the administration of a CD3 binding domain to a patient. The term "caused by" means that the CD3 binding domain is causative for the neurological side effects. The skilled person can easily evaluate whether the administration a CD3 binding domain is causative for a neurological effect or not. To this end, it is just required to closely monitor the patient during the course of the administration and to detect, thereby, that the administration of the CD3 binding domain was causative for the neurological side effects. Likewise, it is envisaged to discontinue the administration of the CD3 binding domain and to evaluate whether the neurological side effects are thereby ameliorated or even fade away, which also indicates that the neurological side effects were caused by said CD3 binding domain.

The term "pentosanpolysulfate (or PPS)", encompasses semi-synthetically produced heparin-like macromolecular carbohydrate derivatives, preferably having the structure of formula (1)

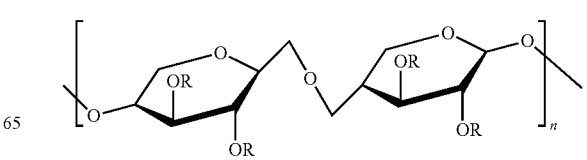

or salt thereof, wherein R represents —SO$_3$Y, and Y is at least one member selected from the group consisting of H and a pharmaceutically acceptable cation such as sodium, potassium, and magnesium.

A preferred PPS is shown in formula (2)

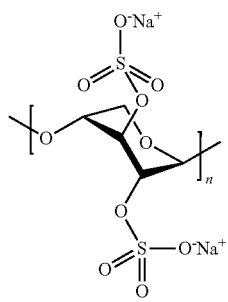

Preferably, n as shown in formula (1) and (2) is such a number so that a PPS has a molecular weight of 4000 to 6000 Dalton.

Another preferred polypentosansulfate encompassed by the present invention is shown in formula (3)

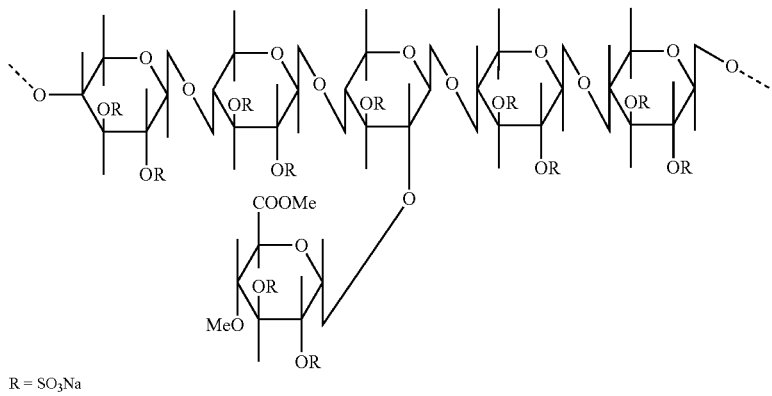

R = SO$_3$Na

In the sense of the present invention, pentosanpolysulfate is a mixture of linear polymers of β1→4-linked xylose, usually sulfated at the 2- and 3-positions and occasionally substituted at the 2-position with 4-O-methyl-α-D-glucuronic acid 2,3-O-sulfate. Accordingly, PPS may also be designated as β-D-Xylan, (1-4), 2,3-bis(hydrogen sulphate).

By way of example, a semi-synthetically produced heparin-like macromolecular carbohydrate derivative such as in particular PPS is, for example, producible (obtainable) as follows: its polysaccharide backbone, xylan is, for example, extracted from the bark of the beech tree or other plant sources and is then treated with sulfating agents such as chlorosulfonic acid or sulfuryl chloride and acid. After sulfation, PPS is usually treated with sodium hydroxide to yield the sodium salt, which is a preferred salt of the present invention. Processes for the production of a semi-synthetically produced heparin-like macromolecular carbohydrate derivative such as in particular PPS are, for example, disclosed in U.S. Pat. No. 2,689,848 or US 2010/0105889.

When administered to a patient of the present invention, PPS may preferably be administered orally, more preferably intravenously. Typical doses are 100, 150, 200 or 300 mg, administered 1-3 times per day, with a maximum amount of 600 mg/d. Typically, the daily dose is between 100 and 600 mg such as 100, 150, 200, 250, 300, 350, 400, 450, 500 mg, 550 or 600 mg or even more. For example, 100 mg PPS may be administered 3-times. Similarly, 200 mg PPS may be administered 2-3-times. Alternatively, 300 mg PPS may be administered 2-times. Alternatively, PPS in an amount, for example, between 100 and 600 such as 100, 150, 200, 250, 300, 350, 400, 450, 500 mg, 550 or 600 mg may be administered over 24 hours via infusion, for example, via a perfusor. In the latter case, a bolus injection of PPS in the amount of, for example, 100 mg may precede the administration before administration of a CD3 binding domain, followed by an administration of PPS of 300 mg over 24 hours.

PPS may be administered prior to (for example, prophylactically, e.g., as a bolus injection), concurrently with or subsequently to the administration of a CD3 binding domain as described herein. Advantageously, PPS can be administered when the dose/amount of a CD3 binding domain that is administered to a patient will be increased. Accordingly, any neurological adverse events could be ameliorated or prevented by this course of action. A particular preferred PPS that is administered to a patient of the present invention is pentosanpolysulfate SP54® commonly known and available in the market (e.g., from bene Arzneimittel GmbH).

An "adverse effect", which is sometimes also denoted as "side effect" or "adverse event (in clinical studies)" is a harmful and undesired effect resulting from medication in the treatment of a patient with a CD3 binding domain. A "neurological adverse effect" which is sometimes also denoted as neurological symptom or CNS adverse effect, includes conditions of a human patient such as all forms of pain, including headache and back pain, muscle weakness or incoordination/disorientation, abnormal sensations, disturbances of the senses, dizziness, seizures, encephalopathy, dysphasia, confusion, ataxia, apraxia, hallucination, headache, aphasia, seizure, speech disorder/impairment, disorientation, palsy, balance disorder, grand mal convulsion, tremor, cerebellar symptoms; includes, in particular, one or more from neurological adverse effects tremor, apraxia, ataxia, aphasia, hallucination and seizure.

Specifically, neurological reactions observed during treatment with a CD3 binding domain include for example confusion and disorientation. "Confusion" as used herein refers to loss of orientation which is the ability to place oneself correctly in the world by time, location, and personal identity, and often memory which is the ability to correctly recall previous events or learn new material. The patients usually have difficulties to concentrate and thinking is not only blurred and unclear but often significantly slowed down. Patients with neurological reactions also suffer from loss of memory. Frequently, the confusion leads to the loss of ability to recognize people and/or places, or to tell time and the date. Feelings of disorientation are common in confusion, and the decision-making ability is impaired. Neurological reactions further comprise blurred speech and/or word finding difficulties. This disorder may impair both, the expression and understanding of language as well as reading and writing. Besides urinary incontinence, also vertigo and dizziness may accompany neurological reactions in some patients.

The herein mentioned "patient" is a mammal, preferably a human, who will be or is (already) treated with a CD3 binding domain.

It is also envisaged that the patient is characterized by a B/T-cell ratio of less than 1:5 (see PCT/EP2010/066207)

In a preferred embodiment, the patient is suspected/assumed to comprise or already comprises malignant CD19 positive lymphocytes (in particular B cells). In the latter case, said patient has already been diagnosed to comprise such cells. These malignant CD19 positive lymphocytes (in particular B cells) are present in a patient developing and/or suffering from leukemia and/or lymphoma.

A "CD3 binding domain" characterizes in connection with the present invention a binding domain which comprises a framework/framework region and an "antigen-binding-site" or "antigen-interaction site" which is able to specifically interact with a CD3 antigen. Said binding/interaction is also understood to define a "specific recognition". The term "specifically interact/interacting" means in accordance with this invention that the binding domain is capable of binding to at least two, preferably at least three, more preferably at least four amino acids of the CD3 antigen, preferably the CD3epsilon antigen, and more preferably the human CD3epsilon antigen. Such CD3 binding domains as well as specific CD3epsilon epitopes are well-known to the skilled person and exemplified in great detail for example in WO2008119567 or in WO2008119566, both of which are included herein by way of reference thereto.

As used herein, "CD3" denotes a molecule expressed as part of the T cell receptor and has the meaning as typically ascribed to it in the prior art. In human, it encompasses in individual or independently combined form all known CD3 subunits, for example CD3 epsilon, CD3 delta, CD3 gamma, CD3 zeta, CD3 alpha and CD3 beta. The human CD3 epsilon is indicated in GenBank Accession No. NM_000733.

A CD3 binding molecule which binds to the human CD3 epsilon is preferred. The CD3epsilon epitope disclosed in great detail in WO2008119567 or in WO2008119566 is even more preferred.

The term "framework (region)" includes a scaffold for antigen-binding sites. For example, such a scaffold could be provided by protein A, in particular, the Z-domain thereof (affibodies), ImmE7 (immunity proteins), BPTI/APPI (Kunitz domains), Ras-binding protein AF-6 (PDZ-domains), charybdotoxin (Scorpion toxin), CTLA-4, Min-23 (knottins), lipocalins (anticalins), neokarzinostatin, a fibronectin domain, an ankyrin consensus repeat domain or thioredoxin (Skerra, Curr. Opin. Biotechnol. 18, 295-304 (2005); Hosse et al., Protein Sci. 15, 14-27 (2006); Nicaise et al., Protein Sci. 13, 1882-1891 (2004); Nygren and Uhlen, Curr. Opin. Struc. Biol. 7, 463-469 (1997)).

A preferred "framework" is, in the context of the present invention, the art-recognized portions of an antibody variable region that exist between the more divergent (i.e., hypervariable) complementarity determining regions (CDRs) within the variable region of an antibody. Such framework regions are typically referred to as frameworks 1 through 4 (FR1, FR2, FR3, and FR4) and provide a scaffold for the presentation of the six CDRs (three from the heavy chain and three from the light chain) in three dimensional space, to form an antigen-binding surface.

A preferred example of a CD3 binding domain in line with the present invention is an antibody. The binding domain may be a monoclonal or polyclonal antibody or derived from a monoclonal or polyclonal antibody. The term "antibody" comprises derivatives or functional fragments thereof which still retain the binding specificity. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The term "antibody" also comprises immunoglobulins (Ig's) of different classes (i.e. IgA, IgG, IgM, IgD and IgE) and subclasses (such as IgG1, IgG2 etc.).

The definition of the term "antibody" also includes embodiments such as chimeric, single chain, de-immunized and humanized antibodies, as well as antibody fragments, like, inter alia, Fab fragments. Antibody fragments or derivatives further comprise F(ab')2, Fv, scFv fragments or single domain antibodies, single variable domain antibodies or immunoglobulin single variable domain comprising merely one variable domain, which might be VH or VL, that specifically bind to an antigen or epitope independently of other V regions or domains; see, for example, Harlow and Lane (1988) and (1999), cited above. Such immunoglobulin single variable domain encompasses not only an isolated antibody single variable domain polypeptide, but also larger polypeptides that comprise one or more monomers of an antibody single variable domain polypeptide sequence.

Bispecific antibody formats are preferred; however other multispecific antibody formats (trispecifc, tetrabodies etc.) are not excluded.

In a further preferred embodiment, the present invention relates to methods of treatment/dosage regimen which employ CD19xCD3 bispecific antibodies, comprising a first binding domain capable of binding to an epitope of human CD3 epsilon chain and a second binding domain capable of binding to human CD19. Examples for bispecific molecules according to the methods of the invention are described in great detail in WO 99/54440 and WO 2004/106381 and WO 2008/119565. All the specific CD19xCD3 bispecific antibodies disclosed therein, including their variants, fragments, equivalents etc. are particularly preferred CD19xCD3 bispecific antibodies of the present invention.

As used herein, a "CD19xCD3 bispecific antibody" (including a CD19xCD3 bispecific single chain antibody) denotes a single polypeptide chain comprising two binding domains. Such single chain antibodies are preferred in the context of the methods/dosage regimen of the present invention. Each binding domain comprises at least one variable region from an antibody heavy chain ("VH or H region"), wherein the VH region of the first binding domain specifically binds to the CD3 epsilon molecule, and the VH region of the second binding domain specifically binds to CD19. The two binding domains are optionally linked to one another by a short polypeptide spacer. A non-limiting example for a polypeptide spacer is Gly-Gly-Gly-Gly-Ser (G-G-G-G-S) and repeats thereof. Each binding domain may additionally comprise one variable region from an antibody light chain ("VL or L region"), the VH region and VL region within each of the first and second binding domains being linked to one another via a polypeptide linker, for example of the type disclosed and claimed in EP 623679 B1, but in any case long enough to allow the VH region and VL region of the first binding domain and the VH region and VL region of the second binding domain to pair with one another such that, together, they are able to specifically bind to the respective first and second binding domains. Such CD19CD3 bispecific single chain antibodies are described in great detail in WO 99/54440 and WO 2004/106381.

The human CD19 protein is indicated in GenBank Accession No. AAA69966.

Preferably, the bispecific antibody applied in the methods/ dosage regimens of the present invention has the domain arrangement VL(CD19)-VH(CD19)-VH(CD3)-VL(CD3).

It is, however, also envisaged that the methods of the invention can be carried out with CD19xCD3 bispecific single chain antibodies of other domain arrangements, such as
VH(CD19)-VL(CD19)-VH(CD3)-VL(CD3),
VL(CD19)-VH(CD19)-VL(CD3)-VH(CD3),
VH(CD19)-VL(CD19)-VL(CD3)-VH(CD3),
VL(CD3)-VH(CD3)-VH(CD19)-VL(CD19),
VH(CD3)-VL(CD3)-VH(CD19)-VL(CD19),
VL(CD3)-VH(CD3)-VL(CD19)-VH(CD19), or
VH(CD3)-VL(CD3)-VL(CD19)-VH(CD19).

A preferred CD19xCD3 bispecific antibody applied in the methods of the present invention comprises the
(a) anti-CD3 CDRs of the heavy chain shown as CD3 CDR-H1 in SEQ ID NO: 11 (RYTMH), more preferably in SEQ ID NO: 11 (GYTFTRYTMH), CD3 CDR-H2 in SEQ ID NO: 12 (YINPSRGYTNYNQKFKD) and CD3 CDR-H3 in SEQ ID NO: 13 (YYDDHYCLDY); and/or
(b) anti-CD3 CDRs of the light chain shown as CD3 CDR-L1 in SEQ ID NO: 14 (RASSSVSYMN), CD3 CDR-L2 in SEQ ID NO: 15 (DTSKVAS) and CD3 CDR-L3 in SEQ ID NO: 16 (QQWSSNPLT); and/or
(c) anti-CD19 CDRs of the heavy chain shown as CD19 CDR-H1 in SEQ ID NO: 17 (SYWMN), more preferably in SEQ ID NO: 17 (GYAFSSYWMN), CD19 CDR-H2 in SEQ ID NO: 18 (QIWPGDGDTNYNGKFKG) and CD19 CDR-H3 in SEQ ID NO: 19 (RETTTVGRYYYAMDY); and/or
(d) anti-CD19 CDRs of the light chain shown as CD19 CDR-L1 in SEQ ID NO: 20 (KASQSVDYDGDSYLN), CD19 CDR-L2 in SEQ ID NO: 21 (DASNLVS) and CD19 CDR-L3 in SEQ ID NO: 22 (QQSTEDPWT).

It is more preferred that the CD19xCD3 bispecific antibody applied in the methods of the present invention comprises the CD3 CDRs of the heavy and light chain. Even more preferably, the CD19xCD3 bispecific antibody applied in the methods of the present invention comprises the CD3 CDRs of the heavy and light chain as well as the CD19 CDRs of the heavy and light chain.

The CDRs referred to herein are in accordance with the Kabat numbering system. The Kabat numbering scheme is a widely adopted standard for numbering the residues in an antibody in a consistent manner (Kabat et al., Sequences of Proteins of Immunological Interest, 1991).

Alternatively, it is preferred that the CD19xCD3 bispecific antibody applied in the methods of the present invention comprises the
(a) CD19 variable heavy chain shown in SEQ ID NO: 3 (nucleotide sequence is shown in SEQ ID NO: 4); and/or
(b) CD19 variable light chain shown in SEQ ID NO: 5 (nucleotide sequence is shown in SEQ ID NO: 6); and/or
(c) CD3 variable heavy chain shown in SEQ ID NO: 7 (nucleotide sequence is shown in SEQ ID NO: 8); and/or
(d) CD3 variable light chain shown in SEQ ID NO: 9 (nucleotide sequence is shown in SEQ ID NO: 10).

More preferably, the CD19xCD3 bispecific antibody applied in the methods of the present invention comprises the CD19 variable heavy and light chain and/or the CD3 variable heavy and light chain. Even more preferably, the CD19xCD3 bispecific antibody applied in the methods of the present invention comprises the CD19 variable heavy and light chain as well as the CD3 variable heavy and light chain.

In another alternative, it is also preferred that said bispecific single chain antibody comprises an amino acid sequence selected from the group consisting of
(a) an amino acid sequence as depicted in SEQ ID NO: 1;
(b) an amino acid sequence encoded by a nucleic acid sequence as shown in SEQ ID NO: 2;
(c) an amino acid sequence encoded by a nucleic acid sequence having at least 70%, 80%, 90%, 95% or 99% identity to a nucleic acid sequence of (b), wherein said amino acid sequence is capable of specifically binding to CD3 and CD19; and
(d) an amino acid sequence encoded by a nucleic acid sequence which is degenerate as a result of the genetic code to a nucleotide sequence of (b), wherein said amino acid sequence is capable of specifically binding to CD3 and CD19.

It is to be understood that the sequence identity is determined over the entire amino acid sequence. For sequence alignments, for example, the programs Gap or BestFit can be used (Needleman and Wunsch J. Mol. Biol. 48 (1970), 443-453; Smith and Waterman, Adv. Appl. Math 2 (1981), 482-489), which is contained in the GCG software package (Genetics Computer Group, 575 Science Drive, Madison, Wis., USA 53711 (1991). It is a routine method for those skilled in the art to determine and identify an amino acid sequence having e.g. 70%, 80%, 90%, 95%, 96%, 97%, 98% or 99% sequence identity to the amino acid sequences of the CD19xCD3 bispecific antibody described herein (preferably MT103). For example, according to Crick's Wobble hypothesis, the 5' base on the anti-codon is not as spatially confined as the other two bases, and could thus have non-standard base pairing. Put in other words: the third position in a codon triplet may vary so that two triplets which differ in this third position may encode the same amino acid residue. Said hypothesis is well known to the person skilled in the art (see e.g. http://en.wikipedia.org/wiki/Wobble_Hypothesis; Crick, J Mol Biol 19 (1966): 548-55). It is furthermore a routine procedure for those skilled in the art to determine cytotoxic activity of such an amino acid sequence having e.g. 70%, 80%, 90%, 95%, 96%, 97%, 98% or 99% sequence identity to the nucleotide or amino acid sequences of the CD19xCD3 bispecific single chain antibody described herein. Cytotoxic activity of the CD19xCD3 bispecific single chain antibody or an antibody construct having e.g. 70%, 80%, 90%, 95%, 96%, 97%, 98% or 99% sequence identity to the amino acid sequences of the CD19xCD3 bispecific single chain antibody can be determined by methods as illustrated e.g. in WO 99/54440.

Particularly preferred, said CD19xCD3 bispecific single chain antibody has the amino acid sequence shown in SEQ ID NO: 1.

Also particularly preferred is the CD19xCD3 bispecific antibody MT103 described in WO 99/54440 as well as those CD19xCD3 bispecific antibodies described in WO 20041106381 and WO 2008/119565

The present invention also relates to a CD19xCD3 bispecific antibody for use in the treatment of malignant CD19 positive lymphocytes in a human patient, wherein said antibody is to be administered prior to, concurrently with or subsequently to the administration of a PPS.

The present invention further relates to a method for
(i) administering a CD19xCD3 bispecific antibody to a human patient, or
(ii) treating malignant CD19 positive lymphocytes in a human patient;
wherein said antibody is to be administered prior to, subsequently to or in combination with PPS.

The administration of the CD3 binding domain, a PPS and/or of (a) pharmaceutical composition(s) comprising either or both of these medical compounds is preferably an intravenous administration. It may be administered as a bolus injection or continually (continuously), with continually being preferred. A continual administration refers to an administration which is essentially without interruption. "Essentially without interruption" includes a continual administration usually without an uninterrupted flow or spatial extension. By way of example, WO 2007/068354 discloses a treatment regimen which is specifically included herein by way of reference thereto. Other treatment regimens which are envisaged in the context of the present invention are disclosed in PCT/EP2010/066207.

It is also envisaged that the human patient of the present invention is characterized by a B/T-cell ratio of less than 1:5 (see PCT/EP2010/066207). As disclosed in great detail in PCT/EP2010/066207, neurological side effects frequently accompany the administration of a CD19xCD3 bispecific antibody in patients which are characterized by a B/T-cell ratio of less than 1:5. The prevention, amelioration or treatment of neurological side effects caused by a CD3 binding domain by way of PPS therapy disclosed herein, is however also applicable to patients which are characterized by a B/T-cell ratio of more than 1:5 (see PCT/EP2010/066207).

The present invention also relates to a (pharmaceutical) kit or package comprising a PPS and/or a CD3 binding domain, and instructions and/or an imprint indicating that the PPS is to be employed for the treatment amelioration and/or prophylaxis of neurological adverse events caused by said CD3 binding domain. Said PPS and CD3 binding domain are preferably packaged together in one sealed package or kit. It is also envisaged that the package or kit of the present invention, further comprises means to administer the PPS and/or CD3 binding domain to a patient and/or buffers, vials, teflon bags or infusion bags which are normally used for the infusion of therapeutic agents. "Means" thereby includes one or more article(s) selected from the group consisting of a syringe, a hypodermic needle, a cannula, a catheter, an infusion bag for intravenous administration, intravenous vehicles, vials, buffers, stabilizers, written instructions which aid the skilled person in the preparation of the respective doses and infusions of the invention etc.

EXAMPLES

The following examples illustrate the invention. These examples should not be construed as to limit the scope of this invention. The examples are included for purposes of illustration and the present invention is limited only by the claims.

A) Patient 109-036 (high risk due to low B:T cell ratio) treated with PPS at start with 5 μg/m$^2$/24 h of Blinatumomab and at escalation to 60 μg/m$^2$/24 h of Blinatumomab after 1 week. Patient was then treated for 7 weeks at 60 μg/m$^2$/24 h of Blinatumomab.

Patient 109-036 was treated with PPS during escalation to 60 μg (100 mg i.v. bolus 3 h±30 min before treatment start and before dose increase (on day 8) immediately followed thereafter for 48 h with a dose of 300 mg/24 h (via perfusor)). Apraxia and aphasia was prevented and patient only showed slight tremor.

Male, 63 y, FL
Stage: III AE
B:T cell ratio: 90:1319
First diagnosis: 12/02
Prior treatment:
   1. 6× CHOP 12/02-04/03
   2. Induction according to Dexa-BEAM Protocol 05/03
   3. Autologous SCT 08/03
Date of last prior treatment: 08/03
Treatment start: 10.5.2010
Major Involvement:
   1. Supraclavicular
   2. Mediastinal
   3. Mesenterial (small intestinal involvement?)
4W CT: PR -63%
8W CT: CRu:-79%
EOS: 30.7.2010
(FL: follicular lymphoma, SCT: stem cell therapy, PR: partial remission, Cru: complete remission (unconfirmed), EOS: end of study).

B) Patient 109-040 (prophylactically) treated with PPS at start with 5 μg/m$^2$/24 h of Blinatumomab and at escalation to 60 μg/m$^2$/24 h of Blinatumomab after 1 week. Patient was then treated for 3 weeks at 60 μg/m$^2$/24 h of Blinatumomab and is then envisaged to be treated for another 4 weeks at 60 μg/m$^2$/24 h of Blinatumomab.

Female, 51 y, LPL, Waldenstroms Disease
IgM 3300 mg/dl, M-Gradient 17.4 g/l
B:T cell ratio: low
First diagnosis: 04/04
Prior treatment: 6× CVP 12/04-03/05
Leukeran mono 10-12/05
R-mono 05-07/06
4× R-CHOP 07/06-10/06
BEAM+autologous SCT 12/06
   Date of last prior treatment: 08/10 Rituximab mono
Treatment start: 11.10.10
Escalation to 60 ug: 18.10.10

The invention claimed is:

1. A method for ameliorating, treating, or preventing adverse neurological events in a patient caused by administering blinatumomab to the patient, the method comprising administering an effective amount of pentosanpolysulfate (PPS) or a pharmaceutically acceptable salt thereof.

2. The method of claim 1, wherein said PPS is pentosanpolysulfate sodium.

3. The method of claim 2, wherein said patient is a human.

4. The method of claim 2, wherein said patient has a B/T-cell ratio of less than 1:5.

5. The method of claim 1, wherein said adverse neurological events is one or more of tremor, apraxia, ataxia, aphasia, hallucination and seizure.

6. The method of claim 5, wherein said patient is a human.

7. The method of claim 5, wherein said patient has a B/T-cell ratio of less than 1:5.

8. The method of claim 1, wherein said patient is a human.

9. The method of claim 1, wherein said patient has a B/T-cell ratio of less than 1:5.

10. The method of claim 1, wherein the PPS is selected from the group consisting of:

(a) a PPS of formula (1)

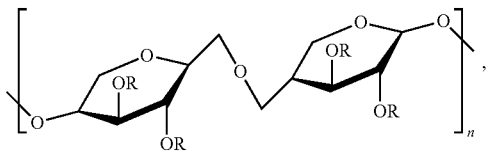

wherein R represents —SO$_3$Y and Y is H or a pharmaceutically acceptable cation;

(b) a PPS of formula (2)

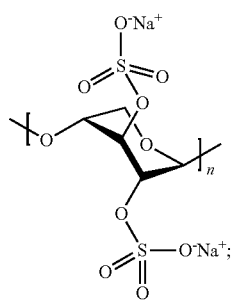

and (c) a PPS of formula (3)

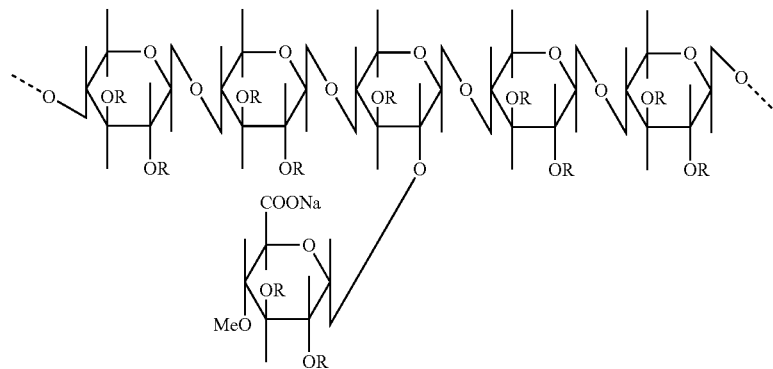

R = SO$_3$Na wherein n as shown in formula (1) and (2) is a number that results in a PPS with a molecular weight of 4000 to 6000 Dalton.

11. The method of claim 10, wherein the pharmaceutically acceptable cation is sodium, potassium, or magnesium.

12. A kit comprising a pentosanpolysulfate (PPS) or a pharmaceutically acceptable salt thereof and blinatumomab and either instructions for administration or an imprint indicating that the PPS or the pharmaceutically acceptable salt thereof is to be employed for ameliorating, treating, or preventing-adverse neurological events caused by blinatumomab.

13. The kit of claim 12, wherein the PPS is selected from the group consisting of:

(a) a PPS of formula (1)

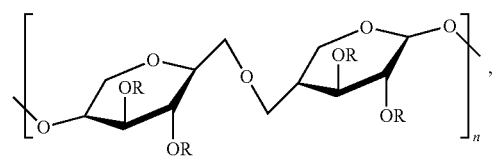

wherein R represents —SO$_3$Y and Y is H or a pharmaceutically acceptable cation;

(b) a PPS of formula (2)

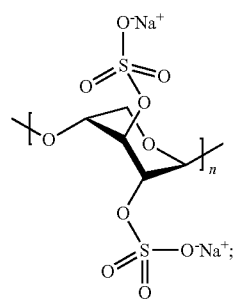

and (c) a PPS of formula (3)
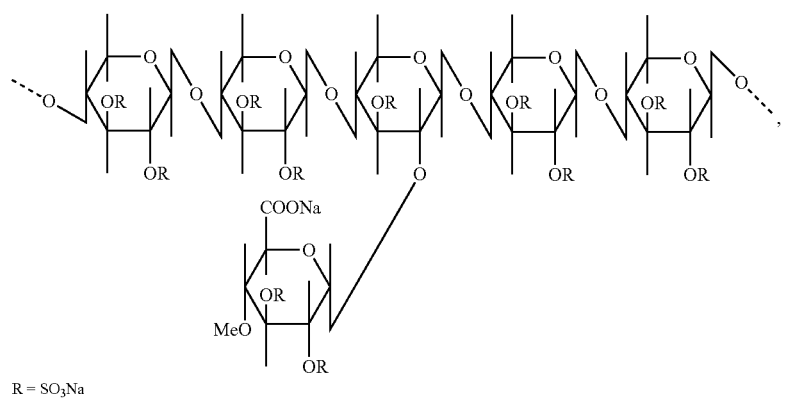
R = SO₃Na
wherein n as shown in formula (1) and (2) is a number that results in a PPS with a molecular weight of 4000 to 6000 Dalton.
14. The kit of claim 13, wherein the pharmaceutically acceptable cation is sodium, potassium, or magnesium.
* * * * *

SEQUENCE LISTING

<160> NUMBER OF SEQ ID NOS: 22

<210> SEQ ID NO 1
<211> LENGTH: 498
<212> TYPE: PRT
<213> ORGANISM: Artificial Sequence
<220> FEATURE:
<223> OTHER INFORMATION: CD19xCD3 bispecific single chain antibody

<400> SEQUENCE: 1

```
Asp Ile Gln Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Ile Gln Leu Thr Gln Ser Pro
385                 390                 395                 400
```

```
Ala Ile Met Ser Ala Ser Pro Gly Glu Lys Val Thr Met Thr Cys Arg
            405                 410                 415

Ala Ser Ser Ser Val Ser Tyr Met Asn Trp Tyr Gln Gln Lys Ser Gly
        420                 425                 430

Thr Ser Pro Lys Arg Trp Ile Tyr Asp Thr Ser Lys Val Ala Ser Gly
    435                 440                 445

Val Pro Tyr Arg Phe Ser Gly Ser Gly Ser Gly Thr Ser Tyr Ser Leu
450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys

<210> SEQ ID NO 2
<211> LENGTH: 1494
<212> TYPE: DNA
<213> ORGANISM: Artificial Sequence
<220> FEATURE:
<223> OTHER INFORMATION: CD19xCD3 bispecific single chain antibody

<400> SEQUENCE: 2
gatatccagc tgacccagtc tccagcttct ttggctgtgt ctctagggca gagggccacc     60
atctcctgca aggccagcca aagtgttgat tatgatggtg atagttattt gaactggtac    120
caacagattc caggacagcc acccaaactc ctcatctatg atgcatccaa tctagtttct    180
gggatcccac ccaggtttag tggcagtggg tctgggacag acttcaccct caacatccat    240
cctgtggaga aggtggatgc tgcaacctat cactgtcagc aaagtactga ggatccgtgg    300
acgttcggtg gagggaccaa gctcgagatc aaaggtggtg gtggttctgg cggcggcggc    360
tccggtggtg gtggttctca ggtgcagctg cagcagtctg ggctgagct ggtgaggcct    420
gggtcctcag tgaagatttc ctgcaaggct tctggctatg cattcagtag ctactggatg    480
aactgggtga agcagaggcc tggacagggt cttgagtgga ttggacagat ttggcctgga    540
gatggtgata ctaactacaa tggaaagttc aagggtaaag ccactctgac tgcagacgaa    600
tcctccagca cagcctacat gcaactcagc agcctagcat ctgaggactc tgcggtctat    660
ttctgtgcaa gacgggagac tacgacggta ggccgttatt actatgctat ggactactgg    720
ggccaaggga ccacggtcac cgtctcctcc ggaggtggtg gatccgatat caaactgcag    780
cagtcagggg ctgaactggc aagacctggg gcctcagtga agatgtcctg caagacttct    840
ggctacacct ttactaggta cacgatgcac tgggtaaaac agaggcctgg acagggtctg    900
gaatggattg gatacattaa tcctagccgt ggttatacta attacaatca gaagttcaag    960
gacaaggcca cattgactac agacaaatcc tccagcacag cctacatgca actgagcagc   1020
ctgacatctg aggactctgc agtctattac tgtgcaagat attatgatga tcattactgc   1080
cttgactact ggggccaagg caccactctc acagtctcct cagtcgaagg tggaagtgga   1140
ggttctggtg gaagtggagg ttcaggtgga gtcgacgaca ttcagctgac ccagtctcca   1200
gcaatcatgt ctgcatctcc aggggagaag gtcaccatga cctgcagagc cagttcaagt   1260
gtaagttaca tgaactggta ccagcagaag tcaggcacct cccccaaaag atggatttat   1320
gacacatcca agtggcttc tggagtccct tatcgcttca gtggcagtgg gtctgggacc   1380
tcatactctc tcacaatcag cagcatggag gctgaagatg ctgccactta ttactgccaa   1440
cagtggagta gtaacccgct cacgttcggt gctgggacca agctggagct gaaa          1494
```

<210> SEQ ID NO 3
<211> LENGTH: 124
<212> TYPE: PRT
<213> ORGANISM: Artificial Sequence
<220> FEATURE:
<223> OTHER INFORMATION: VH anti CD19

<400> SEQUENCE: 3

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120
```

<210> SEQ ID NO 4
<211> LENGTH: 372
<212> TYPE: DNA
<213> ORGANISM: Artificial Sequence
<220> FEATURE:
<223> OTHER INFORMATION: VH anti CD19

<400> SEQUENCE: 4

```
caggtgcagc tgcagcagtc tggggctgag ctggtgaggc ctgggtcctc agtgaagatt      60
tcctgcaagg cttctggcta tgcattcagt agctactgga tgaactgggt gaagcagagg     120
cctggacagg gtcttgagtg gattggacag atttggcctg gagatggtga tactaactac     180
aatggaaagt tcaagggtaa agccactctg actgcagacg aatcctccag cacagcctac     240
atgcaactca gcagcctagc atctgaggac tctgcggtct atttctgtgc aagacgggag     300
actacgacgg taggccgtta ttactatgct atggactact ggggccaagg gaccacggtc     360
accgtctcct cc                                                         372
```

<210> SEQ ID NO 5
<211> LENGTH: 111
<212> TYPE: PRT
<213> ORGANISM: Artificial Sequence
<220> FEATURE:
<223> OTHER INFORMATION: VL anti CD19

<400> SEQUENCE: 5

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60
```

```
Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys
            100                 105                 110

<210> SEQ ID NO 6
<211> LENGTH: 333
<212> TYPE: DNA
<213> ORGANISM: Artificial Sequence
<220> FEATURE:
<223> OTHER INFORMATION: VL anti CD19

<400> SEQUENCE: 6
gatatccagc tgacccagtc tccagcttct ttggctgtgt ctctagggca gagggccacc      60
atctcctgca aggccagcca aagtgttgat tatgatggtg atagttattt gaactggtac     120
caacagattc caggacagcc acccaaactc ctcatctatg atgcatccaa tctagtttct     180
gggatcccac ccaggtttag tggcagtggg tctgggacag acttcaccct caacatccat     240
cctgtggaga aggtggatgc tgcaacctat cactgtcagc aaagtactga ggatccgtgg     300
acgttcggtg agggaccaa gctcgagatc aaa                                   333

<210> SEQ ID NO 7
<211> LENGTH: 119
<212> TYPE: PRT
<213> ORGANISM: Artificial Sequence
<220> FEATURE:
<223> OTHER INFORMATION: VH anti CD3

<400> SEQUENCE: 7

Asp Ile Lys Leu Gln Gln Ser Gly Ala Glu Leu Ala Arg Pro Gly Ala
  1               5                  10                  15

Ser Val Lys Met Ser Cys Lys Thr Ser Gly Tyr Thr Phe Thr Arg Tyr
                 20                  25                  30

Thr Met His Trp Val Lys Gln Arg Pro Gly Gln Gly Leu Glu Trp Ile
             35                  40                  45

Gly Tyr Ile Asn Pro Ser Arg Gly Tyr Thr Asn Tyr Asn Gln Lys Phe
     50                  55                  60

Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 8
<211> LENGTH: 357
<212> TYPE: DNA
<213> ORGANISM: Artificial Sequence
<220> FEATURE:
<223> OTHER INFORMATION: VH anti CD3

<400> SEQUENCE: 8
gatatcaaac tgcagcagtc aggggctgaa ctggcaagac ctggggcctc agtgaagatg      60
tcctgcaaga cttctggcta cacctttact aggtacacga tgcactgggt aaaacagagg     120
```

```
cctggacagg gtctggaatg gattggatac attaatccta gccgtggtta ctactaattac    180 aatcagaagt tcaaggacaa ggccacattg actacagaca aatcctccag cacagcctac    240
atgcaactga gcagcctgac atctgaggac tctgcagtct attactgtgc aagatattat    300
gatgatcatt actgccttga ctactggggc caaggcacca ctctcacagt ctcctca       357
```

```
<210> SEQ ID NO 9
<211> LENGTH: 106
<212> TYPE: PRT
<213> ORGANISM: Artificial Sequence
<220> FEATURE:
<223> OTHER INFORMATION: VL anti CD3

<400> SEQUENCE: 9
```

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

```
<210> SEQ ID NO 10
<211> LENGTH: 318
<212> TYPE: DNA
<213> ORGANISM: Artificial Sequence
<220> FEATURE:
<223> OTHER INFORMATION: VL anti CD3

<400> SEQUENCE: 10
gacattcagc tgacccagtc tccagcaatc atgtctgcat ctccagggga gaaggtcacc     60
atgacctgca gagccagttc aagtgtaagt tacatgaact ggtaccagca gaagtcaggc    120
acctccccca aaagatggat ttatgacaca tccaaagtgg cttctggagt cccttatcgc    180
ttcagtggca gtgggtctgg gacctcatac tctctcacaa tcagcagcat ggaggctgaa    240
gatgctgcca cttattactg ccaacagtgg agtagtaacc cgctcacgtt cggtgctggg    300
accaagctgg agctgaaa                                                   318
```

```
<210> SEQ ID NO 11
<211> LENGTH: 10
<212> TYPE: PRT
<213> ORGANISM: artificial
<220> FEATURE:
<223> OTHER INFORMATION: CD3 CDR-H1

<400> SEQUENCE: 11
```

Gly Tyr Thr Phe Thr Arg Tyr Thr Met His
1               5                   10

```
<210> SEQ ID NO 12
<211> LENGTH: 17
<212> TYPE: PRT
<213> ORGANISM: artificial
```

```
<220> FEATURE:
<223> OTHER INFORMATION: CD3 CDR-H2

<400> SEQUENCE: 12

Tyr Ile Asn Pro Ser Arg Gly Tyr Thr Asn Tyr Asn Gln Lys Phe Lys
1               5                   10                  15
Asp

<210> SEQ ID NO 13
<211> LENGTH: 10
<212> TYPE: PRT
<213> ORGANISM: artificial
<220> FEATURE:
<223> OTHER INFORMATION: CD3 CDR-H3

<400> SEQUENCE: 13

Tyr Tyr Asp Asp His Tyr Cys Leu Asp Tyr
1               5                   10

<210> SEQ ID NO 14
<211> LENGTH: 10
<212> TYPE: PRT
<213> ORGANISM: artificial
<220> FEATURE:
<223> OTHER INFORMATION: CD3 CDR-L1

<400> SEQUENCE: 14

Arg Ala Ser Ser Ser Val Ser Tyr Met Asn
1               5                   10

<210> SEQ ID NO 15
<211> LENGTH: 7
<212> TYPE: PRT
<213> ORGANISM: artificial
<220> FEATURE:
<223> OTHER INFORMATION: CD3 CDR-L2

<400> SEQUENCE: 15

Asp Thr Ser Lys Val Ala Ser
1               5

<210> SEQ ID NO 16
<211> LENGTH: 9
<212> TYPE: PRT
<213> ORGANISM: artificial
<220> FEATURE:
<223> OTHER INFORMATION: CD3 CDR-L3

<400> SEQUENCE: 16

Gln Gln Trp Ser Ser Asn Pro Leu Thr
1               5

<210> SEQ ID NO 17
<211> LENGTH: 10
<212> TYPE: PRT
<213> ORGANISM: artificial
<220> FEATURE:
<223> OTHER INFORMATION: CD19 CDR-H1

<400> SEQUENCE: 17

Gly Tyr Ala Phe Ser Ser Tyr Trp Met Asn
1               5                   10
```

```
<210> SEQ ID NO 18
<211> LENGTH: 17
<212> TYPE: PRT
<213> ORGANISM: artificial
<220> FEATURE:
<223> OTHER INFORMATION: CD19 CDR-H2

<400> SEQUENCE: 18

Gln Ile Trp Pro Gly Asp Gly Asp Thr Asn Tyr Asn Gly Lys Phe Lys
1               5                   10                  15

Gly

<210> SEQ ID NO 19
<211> LENGTH: 15
<212> TYPE: PRT
<213> ORGANISM: artificial
<220> FEATURE:
<223> OTHER INFORMATION: CD19 CDR-H3

<400> SEQUENCE: 19

Arg Glu Thr Thr Thr Val Gly Arg Tyr Tyr Tyr Ala Met Asp Tyr
1               5                   10                  15

<210> SEQ ID NO 20
<211> LENGTH: 15
<212> TYPE: PRT
<213> ORGANISM: artificial
<220> FEATURE:
<223> OTHER INFORMATION: CD19 CDR-L1

<400> SEQUENCE: 20

Lys Ala Ser Gln Ser Val Asp Tyr Asp Gly Asp Ser Tyr Leu Asn
1               5                   10                  15

<210> SEQ ID NO 21
<211> LENGTH: 7
<212> TYPE: PRT
<213> ORGANISM: artificial
<220> FEATURE:
<223> OTHER INFORMATION: CD19 CDR-L2

<400> SEQUENCE: 21

Asp Ala Ser Asn Leu Val Ser
1               5

<210> SEQ ID NO 22
<211> LENGTH: 9
<212> TYPE: PRT
<213> ORGANISM: artificial
<220> FEATURE:
<223> OTHER INFORMATION: CD19 CDR-L3

<400> SEQUENCE: 22

Gln Gln Ser Thr Glu Asp Pro Trp Thr
1               5
```